United States Patent [19]

Frische et al.

[11] Patent Number: 5,312,933
[45] Date of Patent: May 17, 1994

[54] METHOD OF PRODUCING SYMMETRICAL DIFATTY ACID DIAMIDES

[75] Inventors: Rainer Frische, Frankfurt am Main; Jürgen Volkheimer, Wiesbaden; Klaus Wollmann, Eschhofen; Herrmann Schomann, Langen; Judith Schneider; Alexander Ach, both of Frankfurt am Main; Renate Gross-Lannert, Dietzenbach; Bernd Best, Moerfelden, all of Fed. Rep. of Germany

[73] Assignee: Battelle-Institut e.V., Frankfurt am Main, Fed. Rep. of Germany

[21] Appl. No.: 655,456
[22] PCT Filed: Jun. 22, 1990
[86] PCT No.: PCT/EP90/00996
  § 371 Date: Feb. 28, 1991
  § 102(e) Date: Feb. 28, 1991
[87] PCT Pub. No.: WO91/00263
  PCT Pub. Date: Jan. 10, 1991

[30] Foreign Application Priority Data

Jun. 29, 1989 [DE] Fed. Rep. of Germany ....... 3921342

[51] Int. Cl.⁵ .............................................. C07C 231/02
[52] U.S. Cl. ....................................... 554/69; 554/56; 554/68; 554/156; 554/61
[58] Field of Search ................ 554/163, 161, 61, 69, 554/56, 68, 156

[56] References Cited

U.S. PATENT DOCUMENTS 2,844,609 7/1958 Tesoro .
3,388,100 6/1968 Thoma .
4,535,142 8/1985 Brauer .

FOREIGN PATENT DOCUMENTS 21471 1/1981 European Pat. Off. .
1049575 1/1959 Fed. Rep. of Germany .
2434147 2/1975 Fed. Rep. of Germany .
2559698 7/1977 Fed. Rep. of Germany .
2114744 10/1979 Fed. Rep. of Germany .
67117 4/1972 German Democratic Rep. .
209190 4/1984 German Democratic Rep. .
558854 1/1944 United Kingdom .
632242 11/1949 United Kingdom .
1084981 9/1967 United Kingdom .
1153557 5/1969 United Kingdom .

OTHER PUBLICATIONS

Chemical Abstrcts, vol. 80, 15, 1974.
Derwent, CPI, No. 87-141183/20 (1986).
Abstract No. 48459U-DE (1969).
James F. Brower et al., "Decomposition of Aminophylline in Suppository Formulations", Journal of American Sciences, vol. 69, No. 8, pp. 942–944 (Aug. 1980).
Juan Cornejo et al., "Oxidative Degradation of Hydrocortisone in Presence of Attapulgite", American Pharmaceutical Association, vol. 69, No. 8, p. 945 (Aug. 1980).
Von H.-W. Eckert "Kondensationsprodukte aus β-Hydroxyathyläthylendiamin . . . ", Fette, Seifen & Anstrichmittel Nr. 9, pp. 527–533 (1972).
Chemical Abstracts, Abstract No. 221447q, vol. 95 (1981).
Chemical Abstracts, Abstract No. 206453g, vol. 108, (1988).
Chemical Abstracts, Abstract No. 193804a, vol. 101, (1984).
Prof. Dr.-Ing. E.h Dr. Richard Vieweg et al., "Polyurethane" Kunststoff-Handbuch, Band VII, pp. 73, 208, 514 (1986).
Chemical Abstracts, vol. 80, Abstract No. 135205t (1974).
Derwent, CPI, No. 835B/01 (1978).

Primary Examiner—JoséG. Dees
Assistant Examiner—Deborah D. Carr
Attorney, Agent, or Firm—Spencer, Frank & Schneider

[57] ABSTRACT

The present invention relates to a process of producing symmetrically structured difatty acid diamines by reacting mixtures of fatty acids or their esters with diamines, isolating the symmetrical difatty acid diamides from the reaction mixture by making use of their different solubilities and concentrating them by recrystallisation if necessary. The invention also provides for a process of isolating a fatty acid from a mixture of fatty acids wherein the difatty acid diamides produced in the process of the invention are saponified to yield the corresponding free fatty acid.

18 Claims, No Drawings

METHOD OF PRODUCING SYMMETRICAL DIFATTY ACID DIAMIDES

CROSS REFERENCE TO RELATED APPLICATIONS

This application is related to Federal Republic of Germany Application No. P3921342.0, filed Jun. 29, 1989, and International Application No. PCT/EP90/00996, filed Jun. 22, 1990, both of which are incorporated herein by reference.

BACKGROUND OF THE INVENTION

1. Field of the Invention

The invention relates to a method of producing difatty acid diamides of symmetrical composition and/or the corresponding pure fatty acids from fatty acids or fatty acid esters.

2. Technology Review

Difatty acid diamides are compounds with a wide range of technical applications that are used, among other things, as auxiliary materials in plastics processing, as lubricants, or as fluxing agents for solders. Such difatty acid diamides are chiefly made by reacting activated fatty acid mixtures of commercial oils with diamines. The diamides resulting from these kinds of reaction are not uniform compounds in chemical terms. They are rather mixtures of difatty acid diamides as they form according to the various possibilities of combination, depending on the fatty acid composition of the raw materials used. When starting from natural fats and oils, which contain three different kinds of fatty acids, mixtures of six different difatty acid diamides thus result according to the rules of combination, some of which are symmetrical, i.e. are composed of two like fatty acid residues, and others are unsymmetrical. Such difatty acid diamide mixtures of heterogeneous composition can therefore only be used in cases where heterogeneity is not troublesome or is even advantageous. In contrast, pure diolecic acid diamides for example can be used to advantage as lubricating agents for plastics as used, for example, for the sheathing of cables.

Separating fatty acid mixtures usually requires considerable efforts. This is due, among other things, to the structural similarity of the fatty acid molecules to be separated or the reactivity of the frequently preset double bonds. Separation is the more difficult higher purity when purity is required of the end product. Particular problems arise when separating fatty acids of identical chain length which differ only with respect to the number of double bonds. This applies, for example, to the technically very interesting $C_{18}$ carboxylic acids, stearic acid, oleic acid, linoleic acid and linolenic acid. Isolating oleic acid from natural fats is thus very toilsome, because absolute separation from other saturated and unsaturated fatty acids is extremely difficult to achieve. Accordingly, the classical method of producing pure oleic acid by low-temperature crystallization of the fatty acids of olive oil or their methyl esters involves much effort and great losses. However, oleic acid is a very good example by which to demonstrate that a higher content of this constituent, e.g., in cosmetic products like sun lotion, improves the quality of these products considerably.

SUMMARY OF THE INVENTION

The present invention provides for a process of producing symmetrically structured difatty acid diamides comprising reacting mixtures of fatty acids or their esters with diamines, possibly in a suitable solvent and with or without the addition of catalysts and antioxidants; and, separating the symmetrical difatty acid diamides from the resulting reaction mixture by techniques based on differential solubility and, if desired, further purifying said diamides by recrystallization. The invention also provides for a process of isolating a fatty acid from a mixture of fatty acids wherein the difatty acid diamides produced in the process of the invention are saponified to yield the corresponding free fatty acids.

DETAILED DESCRIPTION OF THE INVENTION

An object of the present invention was to provide a method by which it is possible to obtain symmetrically structured difatty acid diamides of such great purity that on one hand they are suitable basic materials for producing high-quality materials such as plastics, as described in the simultaneously filed patent application U.S. Ser. No. 07/659,317, filed Feb. 28, 1991, and on the other hand can be used as initial substance for isolating fatty acids that are difficult to obtain otherwise.

According to the invention this object has been fulfilled by a method of producing symmetrically structured difatty acid diamides or the corresponding pure fatty acids, comprising reacting mixtures of fatty acids or their esters with diamines, possible in a suitable solvent and with or without the addition of catalysts and antioxidants; and, separating the symmetrical difatty acid diamides from the resulting reaction mixture by techniques based on differential solubility and, if desired, further purifying said diamides by recrystallization. The corresponding free fatty acids are then provided by saponification of the separated difatty acid diamides.

Surprisingly it was found that the solubilities and crystallization rates of saturated, unsaturated and hydroxylated fatty acids in organic solvents differ much more than those of the corresponding free acids. The solubility is critically dependent on the functional groups within the fatty acid molecules and follows some fundamental rules.

It has been found that diamides of fatty acid molecules containing an OH group are much less soluble than the diamides of saturated and unsaturated fatty acids. For example, the difatty acid diamides containing 12-hydroxystearic acid, which occur in hydrogenated castor oil are practically insoluble even in boiling methanol. Furthermore, the number of hydroxyl groups influences the solubility to such an extent that dihydroxyl compounds such as bis-12-hydroxystearic acid diamides can be easily separated from those diamide derivatives which contain only a single fatty acid residue with hydroxyl groups. An additional double bond such as for example, in ricinoleic acid, improves the solubility significantly. It has also been observed that the solubility of the relevant diamides increases over that of the diamides of the corresponding saturated fatty acids as a function of the number of double bonds. This makes it easy to separate the unsaturated fatty acids both from saturated fatty acids and from fatty acids bearing hydroxyl groups. The differences are so significant that, although the solubility of fatty acids usually increases with decreasing chain length, even relatively short-chained saturated fatty acids like lauric acid, which occurs in high concentration in palm kernel oil and coconut butter, can be easily separated from $C_{18}$-unsaturated fatty acids in form of their diamides. It has been found further that symmetrically structured difatty acid diamines have a lower solubility combined with a higher crystallization rate than unsymmetrically structured difatty acid diamides, provided the respective elements of the diamides are fatty acids with comparable solubility properties. The solubility of diamides composed of saturated and unsaturated fatty acids lies between the solubilities of diamides consisting only of saturated, or only of unsaturated fatty acids.

Another surprising finding was that overproportionally great amounts of uniformly composed difatty acid diamides result from oils and fats in which one fatty acid predominates in the fatty acid composition. In this respect it is irrelevant what kind of fatty acid it is. If, for example, the fatty acid composition contains 50% oleic acid, the resultant difatty acid diamides include 25% of dioleic acid diamide at the most. If the oleic acid content amounts to roughly 70%, which is the usual concentration in commercial products, a maximum of 49% dioleic acid diamide will form. A mixture of difatty acid damides contains about 80% of uniformly structured dioleic acid diamide when triglycerides are used as initial substance whose fatty acid composition includes 90% oleic acid.

Using the method according to the invention, these findings can be utilized to particularly great advantage for producing symmetrical difatty acid diamides from fatty acid mixtures in which one fatty acid is highly predominant; on the other hand it is possible at the same time to concentrate and isolate rare, extraordinary fatty acids. What is particularly advantageous is that, as is described in the simultaneously filed patent application U.S. Ser. No. 07/659,316, filed Feb. 18, 1991, the reaction with diamines of mixtures of fatty acid esters or fatty acids is not restricted to prepurified fatty acid products, but can also be carried out with crude fats and oils, so that the oils of new plant breeds, for example a new sunflower breed with high oleic acid content or Euphorbia lathyris whose fatty acid composition contains about 85% oleic acid, can also be processed further. In the latter case the resultant difatty acid diamide mixture contains about 70% dioleic acid diamide.

Basically, any mixture of saturated, unsaturated and hydroxylated fatty acids and fatty acid esters can be used for the method according to the invention. Particularly advantageous initial substances are fats and oils of vegetable or animal origin as produced by the usual methods, e.g. cold or hot pressing in worm or screw presses or press extraction. It is advisable that any solid matter that is possibly contained in such raw initial substances, e.g. wood or plant residues, be removed prior to the reaction. Those fats and oils are preferred which have a particularly high content of functional or extraordinary fatty acids. The content of ordinary functional fatty acids should preferably amount to at least 50%, that of extraordinary fatty acids to at least 10%, always related to the total number of fatty acid molecules. Particularly preferred oils are the oil of Euphorbia lathyris, sunflower oil rich in oleic or linoleic acid acid, in particular the "high-oleic" kind of sunflower oil, castor oil or hydrogenated castor oil, linseed oil and rapeseed oils, especially rapeseed oil rich in erucic acid, the oil of Jatropha curcas, olive oil or the oil from marine animals such as fish or whale oil. The initial reaction batch may be varied at will, so that basically the method can be applied both in the laboratory and at the industrial scale.

The respective initial substances can be reacted directly with the diamines. Diamines that can be used are, for example, primary and secondary aliphatic, cyclo-aliphatic, aliphatic-aromatic or aromatic diamines, preferably with 2-44 carbon atoms. This includes also dimeric fatty acids from natural fats and oils for example. Additional structural elements or additional functional groups such as ether groups, amino groups, diamide groupings, ketone groups or sulphone groups may be arranged between the two amino functions in the hydrocarbon chain or at the cyclo-aliphatic or aromatic residue of the diamines. Preferred diamines are 1,2-diaminoethane, 1,3-diaminopropane, 1,6-diaminohexane, 1,8-diaminooctane, piperazine, 4,7,10-trioxatridecane-1,13-diamine, 3,3'-diaminodiphenylsulphone, 3,3'-dimethyl-4,4'-diaminodicyclo-hexylmethane and commercially available ether diamines with the structural formula

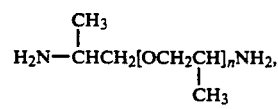

where n is between 1 and 2000. 1,2-diaminoethane and 1,6-diaminohexane are particularly preferable compounds.

The diamines are preferably used in stoichiometric quantities related to the amino functions and fatty acid residues, but the mixing ratio is not overly critical, because even at a twofold excess of amino functions the diamides surprisingly still form prior to the monoamides.

If necessary, an appropriate solvent can be used to ensure a homogeneous course of the reaction. Nonpolar solvents are normally used for this, in particular toluene, xylene or petroleum ether are preferred.

The reaction can occur at temperatures between 20° and 300° C., but the temperature range between 50 and 200° C. is preferred, because in this temperature range the reaction time is a reasonable 1 to 6 hours.

As a precaution, the reaction is carried out in a closed system, e.g. an autoclave. It requires no complicated procedure, but an inert gas atmosphere, e.g. of argon or nitrogen, is preferred because this provides more protection against undesired side-reactions such as oxidation of the initial substances.

If desired, catalysts such as ammonium chloride or toluene-p-sulphonic acid can be added to the reaction mixture. Biological catalysts such as esterases can also be used at the temperatures suited for these enzymes. Other auxiliary agents and additives like polymerisation inhibitors and antioxidants, e.g. ascorbic acid or glucose, can also be added.

When the reaction is completed the reaction products are separated by simple or fractionated crystallization and, if necessary, recrystallized from appropriate solvents. Both polar and non-polar substances can be used as solvents. Recrystallization is preferably done with methanol or ethanol. A simple washing process, for example with toluene or methyl alcohol, is possibly sufficient to obtain pure reaction products A particularly preferred method is hot vapour extraction which also permit the difatty acid diamides to be obtained in crystalline form.

The difatty acid diamides produced by the method according to the invention are of such purity that their further processing presents no problem. Therefore, the difatty acid diamides can either be used directly as additives, for example, for lubricants, or converted into other interesting secondary products. As described in the simultaneously filed patent application U.S. Ser. No. 07/659,717, difatty acid diamides whose fatty acid residues bear function groups such as carbon-carbon double bonds or OH groups, for example the highly concentrated dioleic acid diamides from the crude oil of Euphorbia lathyris or the highly concentrated diricinoleic acid diamides from crude castor oil, can be reacted with appropriate difunctional compounds like diisocyanates and thus constitute new key chemicals for the production of prepolymers, plastics and plastic additives, e.g. for adhesives, sealing materials, foamed plastics, lubricants and a number of other technical auxiliary substances. With the usual saponification methods it is also possible to produce free fatty acids from the difatty acid diamides. These fatty acids can then be derivative or, if they comprise further functional groups, may serve as basic or additive substances for plastics.

According to the invention, however, utilizing the differences in solubility of the diamides permits not only the main fatty acid components of the initial substances to be enriched, but when using the methods of the present invention, those fatty acids which are contained in smaller quantities are also automatically concentrated. By saponification of the concentrated difatty acid diamide mixtures and, if necessary subsequent separation, e.g. by distillation, it is thus possible to produce fatty acid mixtures whose fatty acid composition is clearly different from that of the initial substances. Taking the previously described regularities concerning the solubility of difatty acid diamides into account, the method according to the invention thus makes it possible to change the fatty acid composition of a given initial mixture in a predictable manner, or else, to isolate individual acids that are present only in small quantities.

The easy isolation of symmetrically structured diamides which becomes possible by the method according to the invention increases the industrial usefulness of oils and fats considerably. The method is particularly suitable and efficient for separating fatty acids from mixtures in which one fatty acid is highly predominant and for separating mixtures of the industrially particularly interesting $C_{18}$ fatty acids. Also for the short-chained fatty acids, in particular lauric acid, there is a considerable industrial demand which can be satisfied by the method according to the invention.

Consequently, the invention permits not only the easy synthesis of those fatty acids and their derivatives that have been hard to obtain so far, but it also makes it possible to produce a great number of new key chemicals that so far could not be utilised in the chemical industry because of their difficult availability.

The invention is exemplified in the following examples:

EXAMPLE 1

Reaction of euphorbia oil with 1,2-diaminoethane 100 g euphorbia oil (fatty acid composition: 7% palmitic acid, 2% stearic acid, 84% oleic acid, 3% linoleic acid, 3% linolenic acid) and 9.4 g 1,2-diaminoethane are stirred in a nitrogen atmosphere in an autoclave for three hours at 180° C. and for three hours at 100° C. The product is isolated and recrystallized from methanol. N,N'-ethylene-bisoleodiamide is obtained at a yield of 71 g and with a purity >90%.

EXAMPLE 2

Reaction of linseed oil with 1,2-diaminoethane 9 g linseed oil and 0.9 g 1,2-diaminoethane are stirred in a nitrogen atmosphere in an autoclave for three hours at 180° C. and for three hours at 100° C. The product is recrystallised from 75 ml methanol. While the amides in the mother-liquor are found to be enriched with linoleic and linolenic acid, the amides in the recrystallized product are enriched with oleic acid, palmitic acid and stearic acid.

EXAMPLE 3

Reaction of castor oil with 1,2-diaminoethane 5.1 g castor oil and 0.5 g 1,2-diaminoethane are stirred for 5 hours in an autoclave in a nitrogen atmosphere at 120° C. The reaction product is recrystallised from methanol. The N,N'-ethylene-bisricinoleic acid diamide obtained in this way has a purity >90%.

(Melting point: 83°–85° C.; yield: 2.6 g)

EXAMPLE 4

Reaction of castor oil with 1,6-diaminohexane 51 g castor oil and 9.7 g 1,6-diaminohexane are stirred for 5 hours under nitrogen at 100° C. The reaction product is recrystallized from 150 ml methanol. The hexamethylene-bisricinoleic acid diamide obtained in this way has a purity >90%.

(Melting point: 86°–88° C. yield: 32 g)

EXAMPLE 5

Reaction of hardened castor oil with 1,2-diaminoethane 153 g hardened castor oil and 15 g 1,2-diaminoethane are stirred for 5 hours in an autoclave, in a nitorgen atmosphere at 140° C. The reaction product is recrystalized from methanol. The bis(12-hydroxystearic acid)-N,N'-ethylenediamide obtained in this way has a purity 90%.

(Melting point: 142°–145° C.; yield: 106.5 g)

EXAMPLE 6

Reaction of hardened castor oil with 1,6-diaminohexane 5.1 g hardened castor oil and 0.97 g 1,6-diaminohexane are stirred for 5 hours in an autoclave, in a nitrogen atmosphere at 150° C. The reaction product is subjected to hot vapour extraction with methanol. The bis(12-hydroxystearic acid)-1,6-N,N'-hexamethylene diamide obtained in this way has a purtiy >90%.

(Melting point: 135°–136° C.; yield: 3.7 g)

What is claimed is:

1. A method of producing a symmetrically structured difatty acid diamide or a corresponding pure fatty acid, comprising:

reacting a mixture of fatty acids or their esters with a diamine, to produce a mixture containing a symmetrical difatty acid diamide; and, separating the symmetrical difatty acid diamide from the resulting reaction mixture by recrystallization or fractured crystallization from methanol or ethanol or by hot vapor extraction with methanol based on differential solubility.

2. The method as set forth in claim 1, wherein fats and oils are used as the fatty acids.

3. The method as set forth in claim 1, wherein fats and oils are used as the fatty acid esters.

4. The method as set forth in claim 1, wherein fats and oils comprising at least 50% functional fatty acids are used as the fatty acids or the fatty acid esters.

5. The method as set forth in claim 1, wherein fats and oils comprising at least 10% extraordinary fatty acids are used as the fatty acids or the fatty acid esters.

6. The method as set forth in claim 1 wherein euphorbia oil, high-oleic and high-linoleic sunflower oil, castor oil or hydrogenated castor oil, olive oil, linseed oil, rapeseed oil, the oil of Jatropha curcas or the oil of marine animals is used as the source of fatty acids or fatty acid esters in the reaction mixture.

7. The method as set forth in claim 1, wherein primary and secondary aliphatic, cyclo-aliphatic, aliphatic-aromatic or aromatic diamines are used as the diamine.

8. The method as set forth in claim 1 wherein the diamine is 1,2-diaminoethane or 1,6-diaminohexane.

9. The method as set forth in claim 2, including a solvent is selected from the group consisting of toluene, xylene and petroleum ether.

10. The method as set forth in claim 1 wherein the fatty acids or fatty acid esters and the diamine are reacted at a temperature between 20° C. and 300° C.

11. The method as set forth in claim 1 wherein the mixture of fatty acids or fatty acid esters is reacted with a diamine in an inert gas atmosphere.

12. The method as set forth in claim 1 wherein the reaction mixture additionally comprises ammonium chloride or toluene-p-sulfonic acid as a catalyst.

13. The method as set forth in claim 1, wherein the reaction mixture additionally comprises ascorbic acid or glucose as an antioxidant.

14. The method as set forth in claim 1, wherein the symmetrical difatty acid diamide is separated from the reaction mixture by recrystallization or fractionated crystallization from methanol or ethanol.

15. The method as set forth in claim 1, including purifying said separated symmetrical difatty acid diamide by recrystallization.

16. The method as set forth in claim 1, wherein said reaction mixture includes a solvent.

17. A method of producing a symmetrically structured difatty acid, comprising:

reacting a mixture of fatty acids or their esters with a diamine to produce a mixture containing a symmetrical difatty acid diamide; separating the symmetrical difatty acid diamide from the resulting reaction mixture by recrystallization or fractionated crystallization from methanol or ethanol or by hot vapor with methanol based on differential solubility; and saponifying said separated symmetrical difatty acid diamide.

18. The method as set forth in claim 1 wherein the fatty acids or fatty acid esters and the diamine are reacted at a temperature between 50° C. and 200° C.

* * * * *